United States Patent
Tokunaga et al.

(10) Patent No.: US 7,619,003 B2
(45) Date of Patent: Nov. 17, 2009

(54) PROCESS FOR PRODUCING OPTICALLY ACTIVE COMPOUND

(75) Inventors: Makoto Tokunaga, Hokkaido (JP); Yasushi Tsuji, Hokkaido (JP); Yasushi Obora, Hokkaido (JP); Yoji Hori, Kanagawa (JP); Hiroshi Aoyama, Hokkaido (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 412 days.

(21) Appl. No.: 10/546,858

(22) PCT Filed: Jan. 28, 2004

(86) PCT No.: PCT/JP2004/000729

§ 371 (c)(1),
(2), (4) Date: Aug. 23, 2005

(87) PCT Pub. No.: WO2004/076391

PCT Pub. Date: Sep. 10, 2004

(65) Prior Publication Data

US 2006/0173210 A1  Aug. 3, 2006

(30) Foreign Application Priority Data

Feb. 28, 2003 (JP) ............................. 2003-052187

(51) Int. Cl.
*A61K 31/045* (2006.01)
*A61K 31/19* (2006.01)
(52) U.S. Cl. ...................................... 514/557; 514/578

(58) Field of Classification Search ................. 564/306
See application file for complete search history.

(56) References Cited

FOREIGN PATENT DOCUMENTS

| JP | 06-080617 | 3/1994 |
| JP | 11-313695 | 11/1999 |
| WO | WO-01/89690 A1 | 11/2001 |

OTHER PUBLICATIONS

Mereyala et al., *Tetrahedron*, 53(51):17501-17512 (1997).
Luzzio et al., *Tetrahedron: Asymmetry*, 13:1173-1180 (2002).

*Primary Examiner*—Rebecca L Anderson
*Assistant Examiner*—Shawquia Young
(74) *Attorney, Agent, or Firm*—Edwards Angell Palmer & Dodge LLP; Peter F. Corless; Christine C. O'Day

(57) ABSTRACT

A process for producing an optically active compound based on the hydrolysis of an alkenyl ester compound or the cleavage of an alkenyl ether compound. The process uses neither an acidic compound nor a basic compound, and reactants can be reacted in a high concentration. It does not necessitate a buffer, nutrient, etc. unlike enzymatic reactions or reactions using a microorganism. It is a simple process which attains a satisfactory production efficiency. The process, which is for producing an optically active carboxylic acid or optically active alcohol represented by the general formula (VI): (wherein $R^1$, $R^2$, and $R^3$ are different groups; and A represents methylene, carbonyl, or a single bond), is characterized by causing water to act on an alkenyl ester or alkenyl ether represented by the general formula (I): (wherein $R^4$, $R^5$, and $R^6$ each represents hydrogen, alkyl, etc.) in the presence of a specific transition metal complex having an optically active ligand.

9 Claims, No Drawings

PROCESS FOR PRODUCING OPTICALLY ACTIVE COMPOUND

TECHNICAL FIELD

The present invention relates to a novel process for producing an optically active compound, and particularly to a process for producing an optically active compound by cleaving a carbon-oxygen bond of alkenyl esters or alkenyl ethers by using a metal complex having an optically active ligand as a catalyst.

BACKGROUND ART

Generally, a hydrolysis of vinyl esters and a cleavage of vinyl ethers are conducted in the presence of an acid or basic catalyst. However, this method cannot be used when a functional group or a protective group which is sensitive to an acid or a base is present.

Thus, methods using enzymes or microorganisms other than chemical measures are known as mild methods (see, for example, Prior Art Reference 1).

There are also studies of artificial enzymes to reproduce enzymatic functions by an artificially synthesized molecule though these enzymes are still impractical to use (see, for example, Prior Art Reference 2).

However, in the methods using an enzyme reaction or a reaction using artificial enzyme, substrate concentration is usually about 0.1% to several % by weight. The reaction is therefore conducted in a considerably diluted solution, resulting in low reaction efficiency.

Moreover, in enzyme reactions or reactions using microorganisms, it is necessary for the pH of the solution to be adjusted by using a considerable amount of a buffer solution, and in many reactions, nutrient source is also required.

Examples using metal compounds are also known, i.e., a method in which propenyl ether is cleft in a mild condition by using a palladium compound and a copper compound to obtain alcohols. However, only a racemate can be obtained in this method (see, for example, Prior Art Reference 3).

The prior arts relating to the present invention are as follows, and the following documents are incorporated as reference in this specification.

1. Luzzio. F. A etc., Tetrahedron: Asymmetry, 2002, 1173-1180
2. Zhang. B.; J. Am. Chem. Soc., 1997, 119, 1676-1681
3. Mareyala, H. B. stc., Tetrahedron, Vol. 53, 17501-17512, 1997

DISCLOSURE OF THE INVENTION

An object of the present invention is to provide a process for producing an optical active compound by using a hydrolysis of alkenyl esters and a cleavage of alkenyl ethers, and the process which is simple and has high production efficiency, reacting at high concentrations and necessitating neither a buffer solution nor a nutrient source unlike an enzyme reaction and a reaction using microorganisms

BEST MODE FOR CARRYING OUT THE INVENTION

After intensive studies to solve the problems above, the inventors have found that various metal complexes having an optically active ligand cleave a carbon-oxygen bond in alkenyl esters and alkenyl ethers to obtain an optically active carboxylic acid or alcohol from a racemic raw material, and completed the present invention.

Accordingly, the present invention relates to a process for producing an optically active compound represented by the following formula (VI), the process comprising reacting water with a compound represented by the following formula (I) in the presence of one or more transition metal complexes having, as a ligand, an optically active compound represented by the following formula (II), (III), (IV) or (V):

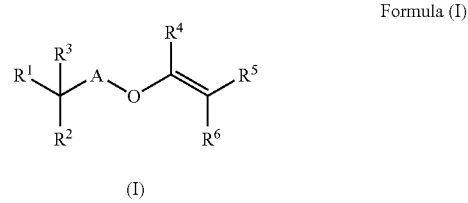

Formula (I)

(wherein $R^1$, $R^2$ and $R^3$, which are different from each other, represent a hydrogen atom, a straight-chain, branched-chain or cyclic alkyl group which may be substituted, a straight-chain, branched-chain or cyclic alkenyl group which may be substituted, a straight-chain or branched-chain alkoxy group which may be substituted, an aralkyl group which may be substituted, an aryl group which may be substituted, a heterocyclic group which may be substituted, a straight-chain or branched-chain alkoxycarbonyl group which may be substituted, an aralkyloxy group which may be substituted, an alkanoyloxy group which may be substituted, an alkylthio group which may be substituted, an aralkylthio group which may be substituted, a benzoyloxy group which may be substituted, a tri-substituted silyloxy group, an amino group which may be substituted, a hydroxyl group, a tetrahydropyran-2-yloxy group or a mercapto group: any two of $R^1$, $R^2$ and $R^3$ may form a ring which may contain a heteroatom therein; and $R^4$, $R^5$ and $R^6$ each independently represent a hydrogen atom, a straight-chain, branched-chain or cyclic alkyl group which may be substituted, a straight-chain, branched-chain or cyclic alkenyl group which may be substituted, an aralkyl group which may be substituted, an aryl group which may be substituted, a heterocyclic group which may be substituted, a straight-chain or branched-chain alkoxycarbonyl group which may be substituted, an aryloxycarbonyl group which may be substituted or an aralkyloxycarbonyl group which may be substituted; $R^4$ and $R^5$ or $R^5$ and $R^6$ may be combined with each other together with an adjacent carbon atom having a double bond to form a ring; and A represents a methylene group, a carbonyl group or a single bond);

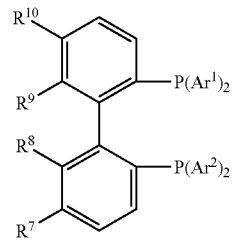

Formula (II)

(wherein $Ar^1$ and $Ar^2$ each independently represent a phenyl group which may be substituted, $R^8$ and $R^9$ each independently represent a methyl group or a methoxy group, and $R^7$ and $R^{10}$ represent a hydrogen atom; $R^7$ and $R^8$ and/or $R^9$ and $R^{10}$ may be combined with each other to form a ring which may contain a heteroatom therein);

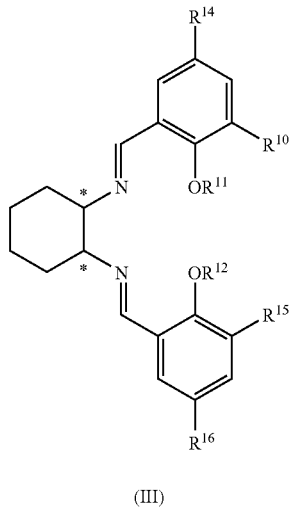

Formula (III)

(III)

(wherein $R^{11}$ and $R^{12}$ each independently represent a hydrogen atom or a methyl group, $R^{13}$, $R^{14}$, $R^{15}$ and $R^{16}$ each independently represent a hydrogen atom or an alkyl group and, * represents an asymmetric carbon atom);

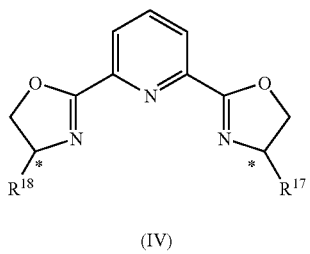

Formula (IV)

(IV)

(wherein $R^{17}$ and $R^{18}$ each independently represent an alkyl group or a phenyl group and,* represents an asymmetric carbon atom);

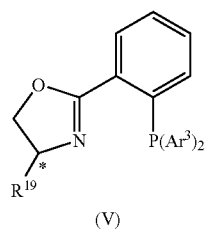

Formula (V)

(V)

(wherein $R^{19}$ represents an alkyl group or a phenyl group, $Ar^3$ represents a phenyl group which may be substituted, and * represents an asymmetric carbon atom), and

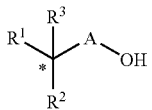

Formula (VI)

(VI)

(wherein $R^1$, $R^2$ and A have the same meanings as above, and * represents an asymmetric carbon atom.)

The present invention is hereinafter explained in detail.

The production process according to the present invention is a process of producing an optically active carboxylic acid or an optically active alcohol represented by the formula (VI) by reacting water with an alkenyl ester or an alkenyl ether represented by the formula (I) in the presence of a transition metal complex having an optically active ligand.

In the formula (I), when A is a carbonyl group, the above process is carried out by the hydrolysis of alkenyl esters to produce an optically active carboxylic acid and when A is a methylene group or a single bond, the process is by the cleavage of alkenyl ethers to produce an optically active alcohol.

In the above formulae (I) and (VI), examples of the alkyl group of the straight-chain, branched-chain or cyclic alkyl group which may be substituted, which is represented by $R^1$, $R^2$ and $R^3$, include straight-chain, branched-chain or cyclic alkyl groups having 1 to 10 carbon atoms, preferably 1 to 6 carbon atoms. Specific examples of these alkyl groups include a methyl group, ethyl group, n-propyl group, isopropyl group, n-butyl group, isobutyl group, sec-butyl group, tert-butyl group, 3,3-dimethyl-2-butyl group, pentyl group, hexyl group, octyl group, decyl group, cyclopropyl group, cyclopentyl group, cyclohexyl group, cyclooctyl group and 2-bornyl group.

Examples of the alkenyl group of the straight-chain, branched-chain or cyclic alkenyl group which may be substituted include straight-chain, branched-chain or cyclic alkenyl groups having 3 to 10 carbon atoms, preferably 3 to 6 carbon atoms. Specific examples of these alkenyl groups include a 2-propenyl group, 2-butenyl group, 1-methyl-3-butenyl group, 5-hexenyl group, 3- or 4-cyclopentenyl group and 3- or 4-cyclohexenyl group.

Examples of the alkoxy group of the straight-chain or branched-chain alkoxy group which may be substituted include straight- or branched-chain alkoxy groups having 1 to 10 carbon atoms, preferably 1 to 6 carbon atoms. Specific examples of these alkoxy groups include a methoxy group, ethoxy group, isopropoxy group, tert-butoxy group, 2,2-dimethylpropoxy group and hexyloxy group.

Examples of the aralkyl group of the aralkyl group which may be substituted include aralkyl groups having 7 to 20 carbon atoms, preferably 7 to 15 carbon atoms. Specific examples of these aralkyl groups include a benzyl group, α-methylbenzyl group, phenethyl group, 4-methylbenzyl group, naphthylmethyl group and naphthylethyl group.

Examples of the aryl group of the aryl group which may be substituted include aryl groups having 6 to 20 carbon atoms, preferably 6 to 14 carbon atoms. Specific examples of the these aryl groups include a phenyl group, tolyl group, xylyl group, naphthyl group, methylnaphthyl group, anthryl group, phenanthryl group and biphenyl group.

Examples of the heterocyclic group of the heterocyclic group which may be substituted include saturated or unsaturated monocyclic, polycyclic or fused heterocyclic groups which have one or more nitrogen atoms, oxygen atoms and/or sulfur atoms in a ring wherein the number of ring members is 5 to 20, preferably 5 to 10 and may be condensed with a carbon cyclic group such as a cycloalkyl group, cycloalkenyl group or aryl group. Specific examples of these heterocyclic groups include a 1,3-dioxolan-4-yl group, 2,2-dimethyl-1,3-dioxolan-4-yl group, 2-oxo-1,3-dioxolan-4-yl group, pyrrolidyl group, piperidyl group, piperidino group, piperazil group, morpholino group, morpholinyl group, pyridyl group, thienyl group, phenylthienyl group, thiazolyl group, oxazolidyl group, furyl group, pyrrolyl group, imidazolyl group, indolyl group, quinolyl group and pyrimidyl group.

Examples of the alkoxycarbonyl group of the alkoxycarbonyl group which may be substituted include straight-chain or branched-chain alkoxycarbonyl groups having 2 to 7 carbon atoms. Specific examples of these alkoxycarbonyl groups include a methoxycarbonyl group, ethoxycarbonyl group, n-propoxycarbonyl group, isopropoxycarbonyl group, n-butyloxycarbonyl group, tert-butyloxycarbonyl group and n-hexyloxycarbonyl group.

Examples of the aralkyloxy group of the aralkyloxy group which may be substituted include aralkyloxy groups having 7 to 20 carbon atoms, preferably 7 to 15 carbon atoms. Specific examples of these aralkyloxy groups include a benzyloxy group, 1-phenetyloxy group and naphthylmethyloxy group.

Examples of the alkanoyloxy group of the alkanoyloxy group which may be substituted include alkanoyloxy groups having 1 to 6 carbon atoms. Specific examples of these alkanoyloxy groups include an acetoxy group, propionyloxy group, pivaloyloxy group and hexanoyloxy group.

Examples of the alkylthio group of the alkylthio group which may be substituted include alkylthio groups having 1 to 4 carbon atoms. Specific examples of these alkylthio groups include a methylthio group, ethylthio group, isopropylthio group and tert-butylthio group.

Examples of the aralkylthio group of the aralkylthio group which may be substituted include aralkylthio groups having 7 to 20 carbon atoms, preferably 7 to 15 carbon atoms. Specific examples of these aralkylthio groups include a benzylthio group, 1-phenetylthio group and naphthylmethylthio group.

The substituents of these alkyl group, alkenyl group, alkoxy group, aralkyl group, aryl group, heterocyclic group and the like, alkoxycarbonyl group, aralkyloxy group, alkanoyloxy group, alkylthio group or aralkylthio group may be any substituent as far as it is no disadvantageous to the reaction according to the present invention. Examples of the substituent include an alkyl group having 1 to 4 carbon atoms, alkoxy group having 1 to 4 carbon atoms, halogen atom, trifluoromethyl group, phenyl group, benzyl group, hydroxyl group, alkoxycarbonyloxy group having 1 to 4 carbon atoms, benzoyl group, benzyloxy group, methoxymethyl group, 2H-tetrahydropyran-2-yloxy group, trimethylsilyloxy group, tert-butyldimethylsilyloxy group, benzyloxycarbonyloxy group, oxirane-2-yl group, 1,3-dioxolan-4-yl group, 2-oxo-1,3-dioxolan-yl group, amino group, dimethylamino group, diethylamino group, acetoxyamino group, benzyloxycarbonylamino group, anilino group and benzylamino group.

Specific examples of the benzoyloxy group which may be substituted, which is represented by $R^1$, $R^2$ and $R^3$ in the above formulae (I) and (VI), include a benzoyloxy group, 4-toluoyloxy group, 4-anisoyloxy group, 4-nitrobenzoyloxy group, 4-chlorobenzoyloxy group and 2,4,6-trichlorobenzoyloxy group.

Specific examples of the tri-substituted silyloxy group include a trimethylsilyloxy group, triethylsilyloxy group, tri-isopropylsilyloxy group, tert-butyldimethylsilyloxy group and triphenylsilyloxy group.

Specific examples of the amino group which may be substituted include an amino group and mono-substituted amino groups such as a methylamino group, ethylamino group and benzylamino group, di-substituted amino group such as a dimethylamino group, diethylamino group and dibenzylamino group, amide groups such as an acetylamino group or benzoylamino group and urethane groups such as a benzyloxycarbonylamino group.

Examples of the ring formed of any two of $R^1$, $R^2$ and $R^3$ include five- or six-membered cycloalkanes having a substituent, $C_7$-$C_{12}$ bicycloalkanes having a substituent, three- to six-membered hetero rings and indane rings.

Examples of five- or six-membered cycloalkanes having a substituent include 2-methylcyclopentane, 2,2-dimethylcyclopentane, 2-tert-butylcyclohexane, 4-tert-butylcyclohexane, 2-phenylcyclohexane, 2-aminocyclopentane, 2-acetylaminocyclohexane, 2-methylaminocyclopentane, 2-hydroxycyclohexane and 2-acetoxycyclohexane. Examples of $C_7$-$C_{12}$ bicycloalkanes having a substituent include 2-norbornane and bornane and examples of the three- to six-membered hetero ring include oxirane, 1,3-dioxolane, 2,2-dimethyl-1,3-dioxolane, 2-oxo-1,3-dioxolane, pyrrolidine ring and piperidine ring. Examples of the indane ring include indane, 1-aminoindane and 1-acetylaminoindane.

In the above formula (I), the definitions and specific examples of the straight-chain, branched-chain or cyclic alkyl group which may be substituted, straight-chain, branched-chain or cyclic alkenyl group which may be substituted, aralkyl group which may be substituted, aryl group which may be substituted, heterocyclic group which may be substituted and alkoxycarbonyl group which may be substituted represented by $R^4$, $R^5$ and $R^6$ are the same as those of the above $R^1$, $R^2$ or $R^3$. Further, the substituents of these alkyl group, alkenyl group, aralkyl group, aryl group, heterocyclic group and alkoxycarbonyl group may be any substituent as far as it is no disadvantageous to the reaction according to the present invention, as well as in $R^1$, $R^2$ and $R^3$. Specific examples of the substituent of these groups are the same as those of the substituent of $R^1$, $R^2$ or $R^3$.

In the above formula (I), examples of the aryloxycarbonyl group of the aryloxycarbonyl group which may be substituted, which is represented by $R^4$, $R^5$ or $R^6$, include aryloxycarbonyl groups having 7 to 15 carbon atoms. Specific examples of the aryloxycarbonyl group which may be substituted include a phenoxycarbonyl group, tolyloxycarbonyl group, xylyloxycarbonyl group, naphthyloxycarbonyl group, methoxyphenyloxycarbonyl group, fluorophenyloxycarbonyl group, trifluoromethylphenyloxycarbonyl group, dimethylaminophenyloxycarbonyl group, acetylaminophenyloxycarbonyl group, methylnaphthyloxycarbonyl group and methoxynaphthyloxycarbonyl group.

Examples of the aralkyloxycarbonyl group of the aralkyloxycarbonyl group which may be substituted include aralkyloxycarbonyl groups having 8 to 16 carbon atoms. Specific examples of the aralkyloxycarbonyl group which may be substituted include a benzyloxycarbonyl group, phenethyloxycarbonyl group, naphthylmethyloxycarbonyl group, α-methylbenzyloxycarbonyl group, 4-methylbenzyloxycarbonyl group and 4-methoxybenzyloxycarbonyl group.

Examples of the ring formed by a combination of $R^4$ and $R^5$ or $R^5$ and $R^6$ together with a carbon atom having a double bond include a cyclopentene ring, cyclohexene ring, cyclooctene ring, 2-bornene ring, 2-norbornene ring, 1-menthene ring and indene ring.

As for the alkenyl esters or alkenyl ethers used as raw materials, which are represented by the formula (I), a commercially available product may be used either as it is or after purified appropriately accordingly, or a compound produced by a known general production method may be used.

Further, the optically active ligand used in the present invention is explained.

One of the optically active ligands to be used in the present invention is an optically active phosphine compound represented by the above formula (II).

Examples of the phenyl group that may be substituted which is represented by $Ar^1$ or $Ar^2$ in the formula (II), include a phenyl group and phenyl groups which may be substituted with an alkyl group having 1 to 4 carbon atoms or alkoxy group having 1 to 4 carbon atoms at one or plural positions.

Examples of the ring where $R^7$ and $R^8$ and/or $R^9$ and $R^{10}$ are combined with each other to form a ring in the formula (II) include a benzene ring, in which a trimethylene group, tetramethylene group, methylenedioxy group or the like may be formed.

Examples of one of the optically active ligands used in the present invention is an optically active salene compound represented by the above formula (III).

Examples of the alkyl group represented by $R^{13}$, $R^{14}$, $R^{15}$ and $R^{16}$ in the formula (III) include lower alkyl groups having 1 to 4 carbon atoms. Specific examples of these lower alkyl groups include a methyl group, ethyl group, n-propyl group, isopropyl group, n-butyl group, isobutyl group, sec-butyl group and tert-butyl group.

A further one of the optically active ligands used in the present invention is an optically active bisoxazoline compound represented by the above formula (IV).

Examples of the alkyl group represented by $R^{17}$ or $R^{18}$ in the formula (IV) include lower alkyl groups having 1 to 4 carbon atoms. Specific examples of these alkyl groups include a methyl group, ethyl group, n-propyl group, isopropyl group, n-butyl group, isobutyl group, sec-butyl group and tert-butyl group.

The remaining one of the optically active ligands used in the present invention is an optically active oxazoline compound represented by the formula (V).

Examples of the phenyl group that may be substituted, which is represented by $Ar^3$ in the formula (V), include a phenyl group and phenyl groups which may be substituted with an alkyl group having 1 to 4 carbon atoms, alkoxy group having 1 to 4 carbon atoms or the like at one or plural positions.

Further, the alkyl group represented by $R^{19}$ include lower alkyl groups having 1 to 4 carbon atoms. Specific examples of these alkyl groups include a methyl group, ethyl group, n-propyl group, isopropyl group, n-butyl group, isobutyl group, sec-butyl group and tert-butyl group.

The transition metal complex used in the production process of the present invention can be easily obtained by mixing and stirring the optically active compound represented by any one of the above formulae (II) to (V) with a transition metal compound in an appropriate solvent which does not react with the compounds in the system under an inert gas atmosphere such as argon or nitrogen, under heating if required, and by treatment according to the conventional method such as concentration, recrystallization and crystallization after the reaction is completed.

Also, the transition metal complex thus obtained according to the present invention may be further reacted with other ligands to make other desired transition metal complexes. The reaction in this case is usually conducted in a solvent at room temperature under the atmosphere. The after treatments and the like after the reaction is the same as above.

The transition metal compounds used in the present invention are preferably compounds of a transition metal of IX group to XII group, more preferably compounds of a transition metal of IX group, X group or XII group. The compounds such as cobalt, palladium, platinum or mercury or the like are particularly preferable.

Preferable examples of the transition metal compound used in the present invention include cobalt compounds, palladium compounds, platinum compounds and mercury compounds as mentioned above. Specific examples of the cobalt compounds include hydrates or non-hydrates of divalent or trivalent cobalt compounds such as cobalt acetate, cobalt acetylacetonate, cobalt chloride, cobalt bromide, cobalt carbonate, cobalt nitrate and cobalt sulfate.

Specific examples of the palladium compound include zero-valent or divalent palladium compounds such as palladium chloride, palladium acetate, dichlorobis(acetonitrile)palladium, dichlorobis(benzonitrile)palladium, dichlorobis(triphenylphosphine)palladium, tris(dibenzylideneacetone)palladium, dichloro(1,5-cyclooctadiene)palladium, palladium bishexafluoropentanedionate and palladium bispentanedionate.

Specific examples of the platinum compound include dichlorobis(acetonitrile)platinum, dichloro(1,5-cyclooctadiene)platinum, chlorotetramine platinum hydrate and potassium tetrachloroplatinate.

Specific examples of the mercury compounds include mercuric acetate, mercuric sulfate and mercuric trifluoroacetate.

The transition metal complex according to the present invention can effect sufficiently when it is used in a catalytic amount based on the alkenyl ester or alkenyl ether which is used as starting material in the production process of the present invention. Further, an optically active compound having higher optical purity may be obtained by using two or more transition metal complexes each consisting of a different metal in combination. Such use is also one of preferable embodiments.

The amount of the transition metal complex according to the present invention is usually 10 mol % enough to satisfy the requirements.

The amount of water used in the production process of the present invention is usually 1 to 10 equivalents, preferably 1 to 5 equivalents based on the alkenyl ester or alkenyl ether.

The reaction according to the present invention usually proceeds in an organic solvent though it proceeds in no solvent insofar as the raw material alkenyl ester or alkenyl ether is not a solid.

Any solvent may be used, and a solvent miscible with water is preferable. However, when the substrate is present in a high concentration, water is made into a separated state and the reaction proceeds even in this state.

Specific examples of the solvent used according to the present invention include, but are not limited to, alcohols such as methanol, ethanol, n-propanol, isopropanol, n-butanol, t-butanol and methoxyethanol, cyclic or non-cyclic ethers such as dioxane, tetrahydrofuran and dimethoxyethane, acetonitrile and N,N-dimethylformamide.

The reaction may not proceed at an advantageous rate at extremely low temperature, and the transition metal complex may be decomposed at extremely high temperature. Therefore, the reaction is usually conducted at 0 to 100° C., preferably at 20 to 90° C.

The reaction time is usually dozens of minutes to dozens of hours, though it differs depending on the type and amount of the alkenyl ester or alkenyl ether used as a raw material, the type and amount of the transition metal complex, the reaction temperature, other conditions and the like.

The reaction according to the present invention proceeds in the presence of oxygen, for example, in the air. However, as for some kinds of raw materials and products which are sensitive to oxygen, it is desirable to induce a reaction under an inert gas atmosphere such as an argon or nitrogen atmosphere, excluding air and oxygen.

The treatment after the reaction can be easily completed in a proper combination of known after treating methods such as filtration, solvent recovery, various chromatographies, distillation and recrystallization, and isolation and purification of products and the like.

According to the present invention, the part unconverted into optically active carboxylic acids or optically active alcohols among the compounds represented by the formula (I) is obtained as optically active compounds represented by the formula (I).

Thus, the production process of the present invention is a process of producing an optically active alkenyl esters or alkenyl ethers represented by the formula (I) as well as process of producing an optically active compound represented by the formula (VI).

It is therefore possible to obtain richer optically active alkenyl esters or alkenyl ethers represented by the formula (I) by conducting a reaction changing various reaction conditions, the type and molar ratio of the complex, the amount of water and the type of solvent appropriately.

All the content described in the specification of Japanese Patent Application No. 2003-52187 is incorporated in this specification.

EXAMPLES

The present invention is described more specifically by the following examples and reference examples, but not limited by these examples and reference examples.

In the following examples, the conversion rate and optical purity were measured by gaschromatography (GC). Gas chromatograph: Ajirent GC-6850 mounted with Capillary-column: CYCLODEX-B (0.25 mmφ×30 m) was used. The product was identified by using a NMR spectrum (Bruker ARX400. Incidentally, the Ph group represents a phenyl group.

Reference Example 1

[(R,R)-N,N'-bis(3,5-di-tert-butylsalicylidene)-1,2-cyclohexanediamine] (hereinafter, referred to as $L^3$ when it is a ligand of a complex) (10.9 g, 20.0 mmol) was dissolved in dichloromethane (80 mL), the solution was added to a methanol solution (80 mL) of cobalt acetate tetrahydrate (5.98 g, 24.0 mmol), the mixture was stirred at room temperature for 15 minutes, and as a result, a red solid was precipitated. After stirred at 0° C. for 30 minutes, the red solid was collected and dried to obtain Co($L^3$) (11.6 g, red solid) (yield: 96%).

Reference Example 2

Two equivalents of acetic acid was added to a Co($L^3$) toluene solution (about 1 M) and the mixture was stirred under the atmosphere. Thereafter, toluene was distilled under reduced pressure to obtain Co(OAc) ($L^3$) in a quantitative yield.

Example 1

A mixture of 360 mg (2 mmol) of 2-bornyl vinyl ether and 16 mg (0.02 mmol) of Hg($L^1$) (OCOCF$_3$)$_2$ was dissolved in 0.5 ml of 2-propanol under the atmosphere, 0.09 mL (5 mmol) of water was added to the mixture, and the mixture was then stirred at room temperature for 45 minutes. The reaction mixture was analyzed By GC, to find that 2-bornyl vinyl ether was converted into an optically active borneol at a conversion rate of 99.8% and with an optical purity of 23% ee.

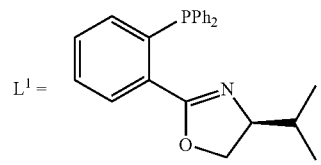

Example 2

A mixture of 336 mg (2 mmol) of vinyl α-methoxyphenylacetate and 14.8 mg (0.04 mmol) of PdCl$^2$($L^2$) was dissolved in 2-propanol under the atmosphere, 0.09 mL (5 mmol) of water was added to the mixture, and the mixture was then stirred at 80° C. for 6 hours. The reaction mixture was analyzed By GC, to find that vinyl α-methoxyphenylacetate was converted into an optically active α-methoxyphenylacetic acid at a conversion rate of 90% and with an optical purity of 12% ee.

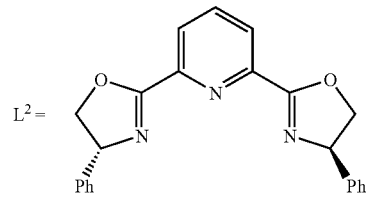

Example 3

168 mg (0.92 mmol) of 2-tert-butylcyclohexyl vinyl ether and 30 mg (0.046 mmol) of Co(OAc) ($L^3$) were dissolved in 0.5 ml of 2-propanol under the atmosphere, 10.7 mg (0.0092 mmol) of [Pt($L^4$) (H$_2$O)$_2$](BF$_4$)$_2$ was added to the mixture. After the mixture was stirred, 45 μL (2.5 mmol) of water was added to the resulting mixture, and the mixture was then heated to 60° C. After 6 hours, the reaction solution was analyzed by GC, to find that 20% of the 2-tert-butylcyclohexyl vinyl ether was left with an optical purity of 80.8% ee and comprised (1R, 2S) isomers. At the same time, 80% of 2-tert-butyrocyclohexanol was produced which had an optical purity of 8.2% ee and comprised (1R, 2S) isomers.

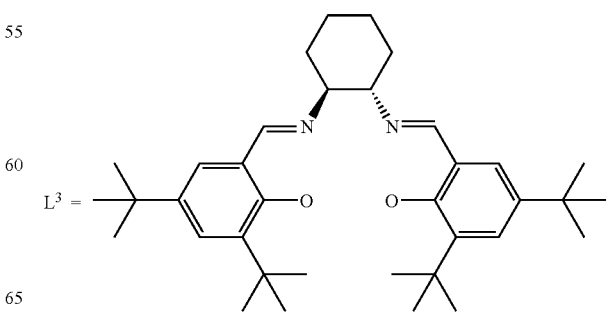

Bound and conjugated with a cobalt atom through oxygen and nitrogen

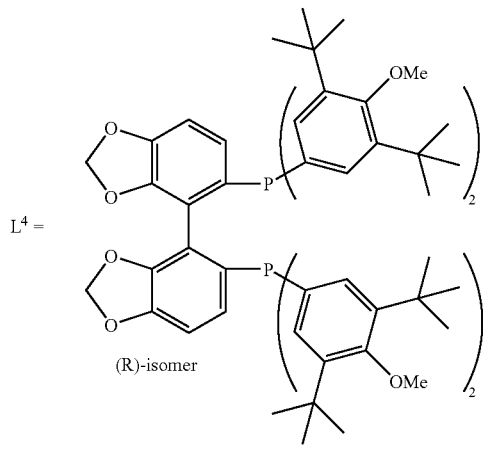

Example 4

91 mg (0.5 mmol) of 2-tert-butylcyclohexyl vinyl ether, 6.6 mg (0.01 mmol) of Co(OAc) ($L^5$) and 1.8 mg (0.01 mmol) of potassium trifluoromethanesulfonate were dissolved in 0.5 ml of 2-propanol under the atmosphere. After the mixture was stirred, 45 μL (2.5 mmol) of water was added to the mixture and the mixture was then heated to 60° C. After 45 hours, the reaction solution was analyzed by GC, to find that 12% of the 2-tert-butylcyclohexyl vinyl ether was left with an optical purity of 91.5% ee and comprised (1S, 2R) isomers. At the same time, 83% of 2-tert-butyrocyclohexanol was produced which had an optical purity of 20% ee and comprised (1R, 2S) isomers.

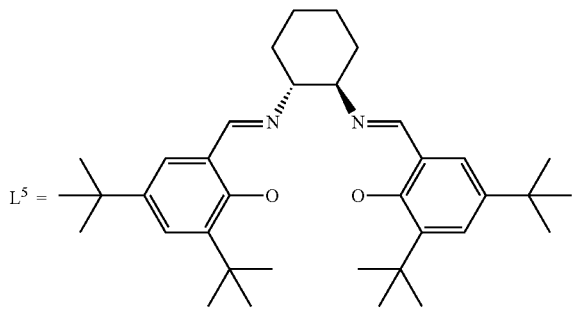

Bound and conjugated with a cobalt atom through oxygen and nitrogen

Example 5

1.09 g (6.00 mmol) of cis-2-tert-butylcyclohexyl vinyl ether and 199 mg (0.30 mmol) of Co(OAc) ($L^3$) were dissolved in 6.0 ml of methanol under the atmosphere and 540 μL (30 mmol) of water was added to the mixture and the mixture was then stirred at 20° C. After 11 hours, the reaction solution was analyzed by GC, to find that 23% of the cis-2-tert-butylcyclohexyl vinyl ether was left with an optical purity of 92% ee and comprised (1R, 2R) isomers. Further, the reaction solution was purified by silica gel column chromatography to isolate the reaction substrate 2-tert-butylcy-clohexyl vinyl ether and the reaction product 2-tert-butylcyclohexanol in a ratio of 22% and 77% respectively. Also, the $k_{rel}$ value showing the selectivity of reactions at this time was 4.9.

The reaction speed ratio $k_{rel}$ of both mirror isomers showing the selectivity was calculated according to the following equation (the same to all the following examples)

$$k_{rel}=ln[(1-conv)(1-ee)]/ln[(1-conv)(1+ee)]$$

(where ee is the excess rate of the unreacted substrate and conv represents a conversion rate of the reaction)

Example 6

The reaction was conducted in the same manner as in Example 5 except that the reaction temperature was altered to –10° C. and the reaction time was altered to 103 hours. The obtained reaction solution was analyzed by GC, to find that 32% of the cis-2-tert-butylcyclohexyl vinyl ether was left with an optical purity of 91% ee. Further, the reaction solution was purified by silica gel column chromatography to obtain the reaction product 2-tert-butylcyclohexanol in a yield of 68%. Also, the $k_{rel}$ value showing the selectivity of reactions at this time was 7.4.

Example 7

The reaction was conducted in the same manner as in Example 5 except that the Co complex was altered to Co($L^3$) and the reaction time was altered to 140 hours. The obtained reaction solution was analyzed by GC, to find that 25% of the cis-2-tert-butylcyclohexyl vinyl ether was left with an optical purity of 94% ee. Further, the reaction solution was purified by silica gel column chromatography to obtain the reaction product 2-tert-butylcyclohexanol in a yield of 75%. Also, the $k_{rel}$ value showing the selectivity of reactions at this time was 5.8.

Reference Example 3

5.8 mg (0.025 mmol) of 2,4-dinitrophenol (containing 20% water) and 15.1 mg (0.025 mmol) of Co($L^3$) were dissolved in 50 μl of toluene and the mixture was stirred at room temperature (20° C.) for 1 hour under the atmosphere. Thereafter, toluene was distilled under reduced pressure to obtain a Co[OC$_6$H$_3$(2,4-(NO$_2$)$_2$)]($L^3$) complex. The obtained complex was used in the following reaction as it was without purified.

Example 8

The Co complex obtained in Reference Example 3 and 91.5 mg (0.50 mmol) of cis-2-tert-butylcyclohexyl vinyl ether were dissolved in 0.5 ml of methanol and 45 μL (2.5 mmol) of water was added to the mixture, and the mixture was then stirred at –10° C. After 77 hours, the reaction solution was analyzed by GC, to find that 38% of the cis-2-tert-butyl-cyclohexyl vinyl ether (1a) was left with an optical purity of 90% ee and comprised (1R, 2R) isomers. Further, the reaction solution was purified by silica gel column chromatography to obtain the reaction product 2-tert-butyrocyclohexanol in a yield of 62%. Also, the $k_{rel}$ value showing the selectivity of reactions at this time was 10.0.

Example 9

The reaction was conducted in the same manner as in Example 8 except that the cleavage reaction temperature of the vinyl ether was altered to 20° C. and the reaction time was altered to 10 hours. The obtained reaction solution was analyzed by GC, to find that 27% of the cis-2-tert-butylcyclohexyl vinyl ether was left with an optical purity of 90% ee. Further, the reaction solution was purified by silica gel column chromatography to obtain the reaction product 2-tert-butyrocyclohexanol in a yield of 73%. Also, the $k_{rel}$ value showing the selectivity of reactions at this time was 5.4.

Example 10

183 mg (1.00 mmol) of DL-menthyl vinyl ether and 19.9 mg (0.030 mmol) of Co(OAc) ($L^3$) were dissolved in 1.0 ml of 2-propanol under the atmosphere and 90 μL (5.0 mmol) of water was added to the mixture, and the mixture was then stirred at −10° C. After 10 hours, the reaction solution was analyzed by GC, to find that 32% of the menthyl vinyl ether was left with an optical purity of 92% ee and comprised (1R, 2S, 5R) isomers. Further, the reaction solution was purified by silica gel column chromatography to isolate the reaction substrate menthyl vinyl ether and the reaction product menthol in a ratio of 28% and 68% respectively. Also, the $k_{rel}$ value showing the selectivity of reactions at this time was 7.8.

Example 11

The reaction was conducted in the same manner as in Example 10 except that the reaction temperature was altered to 20° C. and the reaction time was altered to 3 hours. The obtained reaction solution was analyzed by GC, to find that 32% of the menthyl vinyl ether was left with an optical purity of 79% ee. Further, the reaction solution was purified by silica gel column chromatography to obtain the reaction product menthol in a yield of 68%. Also, the $k_{rel}$ value showing the selectivity of reactions at this time was 4.9.

Example 12

The reaction was conducted in the same manner as in Example 10 except that methanol was used in stead of the solvent 2-propanol, the reaction temperature was altered to 20° C. and the reaction time was altered to 1 hour. The obtained reaction solution was analyzed by GC, to find that 27% of the menthyl vinyl ether was left with an optical purity of 58% ee. Further, the reaction solution was purified by silica gel column chromatography to obtain the reaction product menthol in a yield of 73%. Also, the $k_{rel}$ value showing the selectivity of reactions at this time was 2.5.

Example 13

The reaction was conducted in the same manner as in Example 10 except that methanol was used instead of the solvent and the reaction time was altered to 2 hours. The obtained reaction solution was analyzed by GC, to find that 12% of the menthyl vinyl ether was left with an optical purity of 76% ee. Further, the reaction solution was purified by silica gel column chromatography to obtain the reaction product menthol in a yield of 88%. Also, the $k_{rel}$ value showing the selectivity of reactions at this time was 2.3.

Example 14

62.4 mg (0.20 mmol) of O-vinylnaphthol and 1.3 mg (0.002 mmol) of Co (OAc) ($L^3$) were dissolved in 50 μl of methanol under the atmosphere, 18 μl (1.0 mmol) of water was added to the mixture, and the mixture was then stirred at −10° C. After 5 hours, the reaction solution was analyzed by HPLC, to find that 89% of the O-vinylnaphthol was left with an optical purity of 10% ee. Further, the reaction solution was purified by silica gel column chromatography to obtain the reaction product binaphthol in a yield of 11%. Also, the $k_{rel}$ value showing the selectivity of reactions at this time was 11.0.

Example 15

30.4 mg (0.086 mmol) of 2-acetyloxy-2'-vinyloxy1,1'-binaphthyl and 2.8 mg (0.004 mmol) of Co (OAc) ($L^3$) were dissolved in 90 μl of a mixed solvent (2:1) of methanol and THF under the atmosphere and 8 μl (0.44 mmol) of water was added to the mixture, and the mixture was then stirred at 0° C. After 10 hours, the reaction solution was analyzed by HPLC, to find that 66% of the 2-acetyloxy-2'-vinyloxy1,1'-binaphthyl was left with an optical purity of 44% ee. Further, the reaction solution was purified by silica gel column chromatography to obtain the reaction product O-acetylbinaphthol in a yield of 34%. Also, the $k_{rel}$ value showing the selectivity of reactions at this time was 20.7.

Example 16

95.8 mg (0.27 mmol) of 2-acetyloxy-2'-vinyloxy1,1'-binaphthyl and 9.0 mg (0.014 mmol) of Co(OAc) ($L^3$) were dissolved in 0.27 ml of a mixed solvent (2:1) of methanol and THF under the atmosphere, 25 μl (1.44 mmol) of water was added to the mixture, and the mixture was then stirred at 0° C. After 21 hours, the reaction solution was purified by silica gel column chromatography and as a result, 34% of 2-acetyloxy-2'-vinyloxy-1,1'-binaphthyl was left with an optical purity of 86% ee measured by HPLC. The reaction product O-acetylbinaphthol was obtained in a yield of 66%. Also, the $k_{rel}$ value showing the selectivity of reactions at this time was 6.6.

Example 17

The reaction was conducted in the same manner as in Example 16 except that 2-tert-butyldiphenylsilyloxy-2'-vinyloxy-1,1'-binaphthyl was used instead of 2-acetyloxy-2'-vinyloxy-1,1'-binaphthyl, the reaction temperature was altered to 20° C. and the reaction time was altered to 22 hours. The reaction solution was purified by silica gel column chromatography and as a result, 67% of the 2-tert-butyldiphenylsilyloxy-2'-vinyloxy-1,1'-binaphthyl was left with an optical purity of 38% ee. Also, the reaction product O-acetylbinaphthol was obtained in a yield of 33%. Also, the $k_{rel}$ value showing the selectivity of reactions at this time was 12.7.

INDUSTRIAL APPLICABILITY

The present invention provides a process of producing an optically active compound by utilizing a hydrolysis of alkenyl esters or a cleavage of alkenyl ethers. The reaction can be conducted in a high concentration, unnecessary to use an acidic compound or a basic compound, also unnecessary to use a buffer solution or nutrient sources unlike an enzymatic reaction and a reaction using microorganisms and an optically active carboxylic acid or alcohol can be easily obtained from a raw material of racemic isomer.

Further, according to the production process of the present invention, optically active alkenyl esters or alkenyl ethers can be produced, and it is also possible to obtain the optically active alkenyl esters or alkenyl ethers richer by conducting a reaction changing various reaction conditions, the type and molar ratio of the complex, the amount of water and the type of solvent appropriately.

The invention claimed is:

1. A process for producing an optically active compound represented by the following formula (VI), the process comprising reacting water with a compound represented by the following formula (I) in the presence of one or more transition metal complexes having, as a ligand, an optically active compound represented by the following formula (III):

Formula (I)

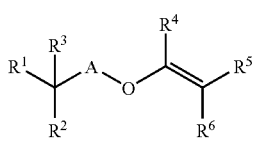

wherein $R^1$, $R^2$ and $R^3$, which are different from each other, represent a hydrogen atom, a straight-chain, branched-chain or cyclic alkyl group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, a straight-chain or branched-chain alkoxy group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, an aralkyl group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, an aryl group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, an aralkyloxy group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, an alkylthio group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, or an aralkylthio group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine;

any two of $R^1$, $R^2$ and $R^3$ optionally form a ring; and $R^4$, $R^5$ and $R^6$ each independently represent a hydrogen atom, or a straight-chain, branched-chain or cyclic alkyl group optionally substituted with alkyl, alkoxy, halogen, trifluoromethyl, phenyl, benzyl, hydroxyl, alkoxycarbonyloxy, benzoyl, benzyloxy, methoxymethyl, 2H-tetrahydropyran-2-yloxy, trimethylsilyloxy, tert-butyldimethylsilyloxy, benzyloxycarbonyloxy, oxirane-2-yl, 1,3-dioxolan-4-yl, 2-oxo-1,3-dioxolan-yl, amino, dimethylamino, diethylamino, acetoxyamino, benzyloxycarbonylamine, aniline or benzylamine, $R^4$ and $R^5$ or $R^5$ and $R^6$ are optionally combined with each other together with an adjacent carbon atom having a double bond to form a ring; and A represents a carbonyl group or a single bond;

Formula (III)

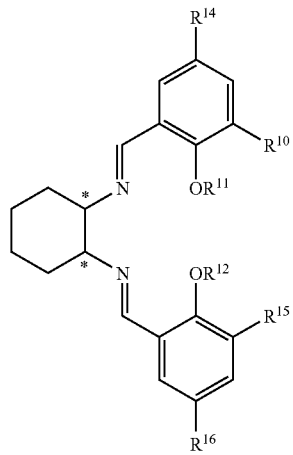

wherein $R^{11}$ and $R^{12}$ each independently represent a hydrogen atom or a methyl group, $R^{13}$, $R^{14}$, $R^{15}$ and $R^{16}$ each independently represent a hydrogen atom or an alkyl group and, * represents an asymmetric carbon atom;

Formula (VI)

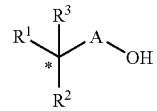

wherein $R^1$, $R^2$ and A have the same meanings as above, and * represents an asymmetric carbon atom.

2. A production process according to claim 1, wherein A is a carbonyl group in the formulae (I) and (VI).

3. A production process according to claim 1, wherein A is a single bond in the formulae (I) and (VI).

4. A production process according to claim 1, wherein the transition metal complex is a complex of a transition metal of IX to XII groups in the periodic table.

5. A production process according to claim 4, wherein the complex of the transition metal of IX to XII groups in the periodic table is a complex of a transition metal of IX, X or XII group.

6. A production process according to claim 5, wherein the transition metal of IX group in the periodic table is cobalt.

7. A production process according to claim 5, wherein the transition metal of X group in the periodic fable is palladium or platinum.

8. A production process according to claim 5, wherein the transition metal of XII group in the periodic table is mercury.

9. A production process according to claim 1, wherein the reaction is conducted in an organic solvent.

* * * * *